US010524922B2

(12) United States Patent
Courtney, Jr. et al.

(10) Patent No.: US 10,524,922 B2
(45) Date of Patent: Jan. 7, 2020

(54) GLENOID IMPLANT ANCHOR POST

(71) Applicant: Tornier, Inc., Edina, MN (US)

(72) Inventors: Robert Courtney, Jr., Pierceton, IN (US); Austin W. Mutchler, Warsaw, IN (US); R. Sean Churchill, Mequon, WI (US)

(73) Assignee: Tornier, Inc., Bloomington, MN (US)

( * ) Notice: Subject to any disclaimer, the term of this patent is extended or adjusted under 35 U.S.C. 154(b) by 0 days.

(21) Appl. No.: 15/379,359

(22) Filed: Dec. 14, 2016

(65) Prior Publication Data

US 2017/0095340 A1    Apr. 6, 2017

Related U.S. Application Data

(62) Division of application No. 12/398,750, filed on Mar. 5, 2009, now Pat. No. 9,545,311.

(51) Int. Cl.
  *A61F 2/40* (2006.01)
  *A61F 2/30* (2006.01)
  *A61F 2/36* (2006.01)

(52) U.S. Cl.
  CPC .. *A61F 2/4081* (2013.01); *A61F 2002/30604* (2013.01); *A61F 2002/30822* (2013.01);
  (Continued)

(58) Field of Classification Search
  USPC .......................................... 623/19.11–19.13
  See application file for complete search history.

(56) References Cited

U.S. PATENT DOCUMENTS 3,896,504 A * 7/1975 Fischer .................... A61F 2/32
                                                              411/38
4,725,280 A    2/1988 Laure
          (Continued)

FOREIGN PATENT DOCUMENTS

EP       0776636       6/1997
EP       1013246       11/1999
          (Continued)

OTHER PUBLICATIONS

European Search Report Issued in EP Application No. 10155440 dated Aug. 9, 2010.
(Continued)

*Primary Examiner* — David H Willse
*Assistant Examiner* — Javier G Blanco
(74) *Attorney, Agent, or Firm* — Knobbe, Martens, Olson & Bear, LLP

(57) ABSTRACT

A prosthesis that mechanically couples with both cancellous bone and cortical bone of a glenoid includes a head portion comprising a rear surface and an articular surface, an anchor member, and a plurality of deformable fins extending radially outward from the anchor member. The anchor member includes a distal end and a proximal end connected to the rear surface of the head portion. The plurality of deformable fins extend radially outward from the anchor member and includes at least a first proximal fin adjacent to the rear surface of the head portion positioned to engage with the cortical bone. The anchor member may also include at least one distal fin located proximate the distal end of the anchor member positioned to engage with the cancellous bone.

11 Claims, 15 Drawing Sheets

(52) U.S. Cl.
CPC ............ *A61F 2002/30828* (2013.01); *A61F 2002/30878* (2013.01); *A61F 2002/30881* (2013.01); *A61F 2002/30884* (2013.01); *A61F 2002/30892* (2013.01); *A61F 2002/30897* (2013.01); *A61F 2002/3666* (2013.01)

(56) References Cited

U.S. PATENT DOCUMENTS

| | | | |
|---|---|---|---|
| 5,032,132 | A | 7/1991 | Matsen, III et al. |
| 5,080,673 | A | 1/1992 | Burkhead et al. |
| 5,108,446 | A | 4/1992 | Wagner et al. |
| 5,662,657 | A | 9/1997 | Carn |
| 5,702,447 | A * | 12/1997 | Walch .................. A61B 17/809 606/309 |
| 5,776,202 | A * | 7/1998 | Copf ..................... A61F 2/4225 623/18.11 |
| 5,800,551 | A * | 9/1998 | Williamson ....... A61B 17/1659 623/19.11 |
| 6,699,289 | B2 | 3/2004 | Iannotti et al. |
| 6,911,047 | B2 | 6/2005 | Rockwood, Jr. et al. |
| 7,160,328 | B2 | 1/2007 | Rockwood, Jr. et al. |
| 2001/0037153 | A1 | 11/2001 | Rockwood, Jr. et al. |
| 2003/0055507 | A1 | 3/2003 | McDevitt et al. |
| 2007/0055380 | A1 | 3/2007 | Berelsman et al. |
| 2007/0142917 | A1 * | 6/2007 | Roche ................... A61F 2/4081 623/19.11 |
| 2007/0219638 | A1 * | 9/2007 | Jones .................... A61F 2/4081 623/19.11 |
| 2009/0192621 | A1 * | 7/2009 | Winslow .................. A61F 2/40 623/19.14 |
| 2009/0292364 | A1 * | 11/2009 | Linares ................ A61B 17/686 623/19.13 |
| 2010/0228352 | A1 | 9/2010 | Courtney, Jr. |

FOREIGN PATENT DOCUMENTS

| | | | | |
|---|---|---|---|---|
| EP | 1064890 | | 1/2001 | |
| FR | 2843293 | A1 * | 2/2004 | .......... A61F 2/4081 |
| FR | 2937245 | A1 * | 4/2010 | .......... A61F 2/4081 |
| FR | 2 955 247 | | 8/2010 | |

OTHER PUBLICATIONS

Countless Fixation, Using a Polyethylene Oseo-Integration Peg as Used on the Freeman-Samuelson Knee, brochure, 20 pages.

* cited by examiner

GLENOID IMPLANT ANCHOR POST

CROSS-REFERENCE TO RELATED APPLICATION

This application is a divisional of U.S. patent application Ser. No. 12/398,750, filed Mar. 5, 2009, the entire contents of which are hereby incorporated by reference herein.

TECHNICAL FIELD

The present invention relates generally to an apparatus and device for securing a glenoid implant to a glenoid, and in particular, to an anchor with deformable portions that are adapted to form a cement-less connection with the glenoid.

BACKGROUND OF THE INVENTION

In a healthy shoulder joint, the humeral head of the humerus interacts with the glenoid of the scapula to form a "ball and socket" joint. The humeral head abuts and articulates with the glenoid to allow a wide range of motion in the shoulder. In an unhealthy shoulder joint, the interaction between the glenoid and the humerus are compromised, requiring repair or replacement. Total shoulder replacement is one method used to replace shoulder joints that have been damaged beyond repair due to trauma or disease. Typically, a total shoulder replacement procedure includes providing a glenoid component and a humeral component that interact with each other at an articulating surface.

Conventionally, glenoid components have been designed as two-piece components made of plastic and metal. Due to difficulties in designing a mechanism to lock the two pieces together, the assembly can fail over time. Replacement of the glenoid component requires that the patient undergo an additional surgical procedure and be subjected to additional recovery time and costs. One-piece glenoid components have also been developed that fixate to a glenoid and provide an articulating surface for the humeral component. Bone cement is commonly used to secure the glenoid component to the glenoid for both two-piece and one-piece components.

U.S. Pat. No. 6,911,047 (Rockwood Jr. et al.) discloses a glenoid component having an anchor peg and stabilizing pegs to secure the glenoid component to a glenoid without the use of bone cement. The anchor peg disclosed in Rockwood Jr. et al. includes a body portion having a plurality of fins at a proximal end of the body portion. When the glenoid component is positioned within the glenoid and scapula, the fins provide resistance to removal forces on the glenoid component. The stabilizing pegs are positioned within the glenoid around the anchor peg to prevent movement of the body portion relative to the glenoid.

BRIEF SUMMARY OF THE INVENTION

The present invention is directed to a prosthesis with an anchor having deformable portions that engage with cortical bone at a glenoid.

In some embodiments, the present prosthesis is adapted to form a cement-less connection with a glenoid. The deformable portions are optionally structured for substantially unidirectional deformation. That is, the deformable portions resist deformation in the direction of removal. The anchor is optionally modular so that it is easily customized for patients of varying sizes. For example, different patients may have cortical bone of varying thicknesses and/or glenoids of varying depths.

In one embodiment, the present invention is a prosthesis that mechanically couples with both cancellous bone and cortical bone of a glenoid. The prosthesis includes a head portion comprising a rear surface and an articular surface, an anchor member, and a plurality of deformable fins extending radially outward from the anchor member. The anchor member includes a proximal end and a distal end. The proximal end is connected to the rear surface of the head portion. The plurality of deformable fins extend radially outward from the anchor member and include at least a first proximal fin adjacent to the rear surface of the head portion positioned to engage with the cortical bone. The plurality of deformable fins may also include at least one distal fin located proximate the distal end of the anchor member positioned to engage with the cancellous bone.

In another embodiment, the present invention is a prosthesis for securement to a glenoid and includes a head portion and an anchor. The head portion has a first surface and a second surface. The anchor extends from the first surface of the head portion and includes a proximal end connected to the first surface of the head portion, a distal end opposite the proximal end and a set of proximal fins. The set of proximal fins extend radially from the proximal end of the body portion. The anchor may also include a set of distal fins extending radially from the distal end of the body portion. The anchor is configured to engage the glenoid.

In an alternative embodiment, the present invention is an implant positionable between a glenoid and a humeral component. The implant includes a head portion and an anchor. The head portion has a first surface engageable with the glenoid and a second surface engageable with the humeral component. The anchor extends substantially perpendicularly from the first surface of the head portion and has a first end attached to the first surface, a second end opposite the first end, and a first set of flexible flanges positioned proximate the first end of the anchor. The anchor may also include a second set of flexible flanges positioned proximate the second end of the anchor.

The present invention is also directed to a method of fixating a prosthesis to a glenoid. The method includes aligning an anchor of the prosthesis with a bore formed in the glenoid and inserting the anchor in the bore such that a first surface of the prosthesis engages the glenoid. The anchor includes a first deformable fin and a second deformable fin. The first deformable fin is implanted within cancellous bone and the second deformable fin is implanted proximate cortical bone.

Terminology such as "first," "second," "third," etc., is used herein to designate particular components being described. Because various components of the embodiments described herein can be positioned in a number of different orientations and in a number of different sequences, this terminology is used for the purposes of illustration and is not intended to be read in a restrictive manner.

DETAILED DESCRIPTION OF THE INVENTION

Figure 1:
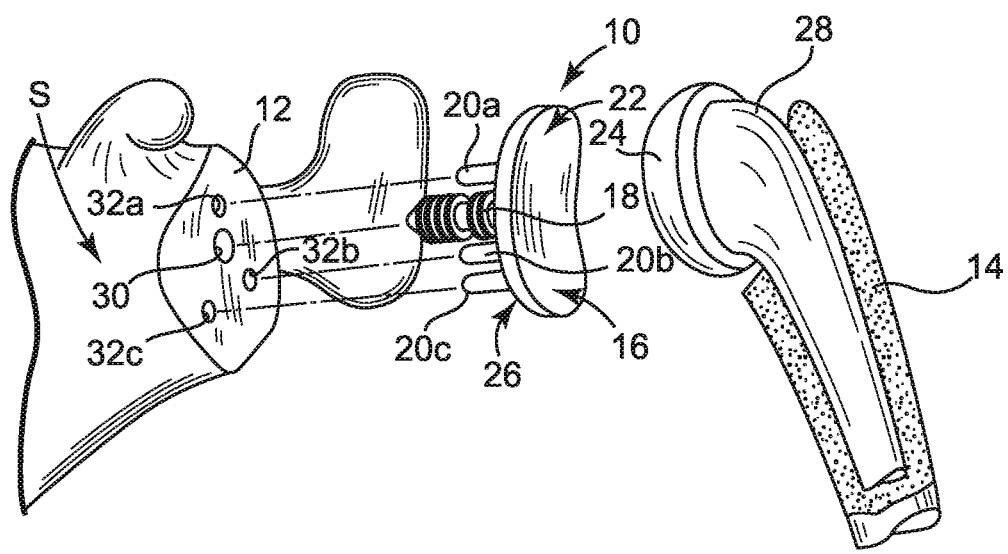
FIG. 1 is an exploded view of a glenoid component positioned between a glenoid and a humeral component in accordance with an embodiment of the present invention.

FIG. 1 shows an exploded view of a glenoid component 10 positioned between a glenoid 12 of a scapula S and a humeral component 14. While the humeral component 14 illustrated in FIG. 1 is a prosthesis, the present glenoid component 10 can also engage with an anatomical humeral head. Therefore, reference to the humeral component 14 herein should be construed to include an anatomical humeral head.

The glenoid component 10 is attachable to the glenoid 12 and functions as an artificial surface for engagement with the humeral component 14. The glenoid component 10 can be secured to the scapula S without the use of bone cement and provides structural resistance from being removed from the scapula S.

The glenoid component 10 includes a head portion 16, an anchor 18, a first stabilizing pin 20a, a second stabilizing pin 20b and a third stabilizing pin 20c (collectively referred to as "stabilizing pins 20"). The head portion 16 includes a first articulating surface 22 and a second surface 26. The first articulating surface 22 engages the humeral head 24 of the humeral component 14, which includes a stem 28 implanted in a humerus H, to allow rotation and movement of a shoulder.

The anchor 18 and stabilizing pins 20 of the glenoid component 10 extend from the second surface 26 of the head portion 16 of the glenoid component 10 and secure the glenoid component 10 to the glenoid 12. In the illustrated embodiment, the glenoid 12 and scapula S include an anchor hole 30 and a plurality of stabilizing holes 32a, 32b, 32c (referred to collectively as "32") to accept the anchor 18 and the stabilizing pins 20, respectively. In an alternate embodiment, the present glenoid component 10 can be implanted without the pre-drilled holes 30, 32.

Figure 2:
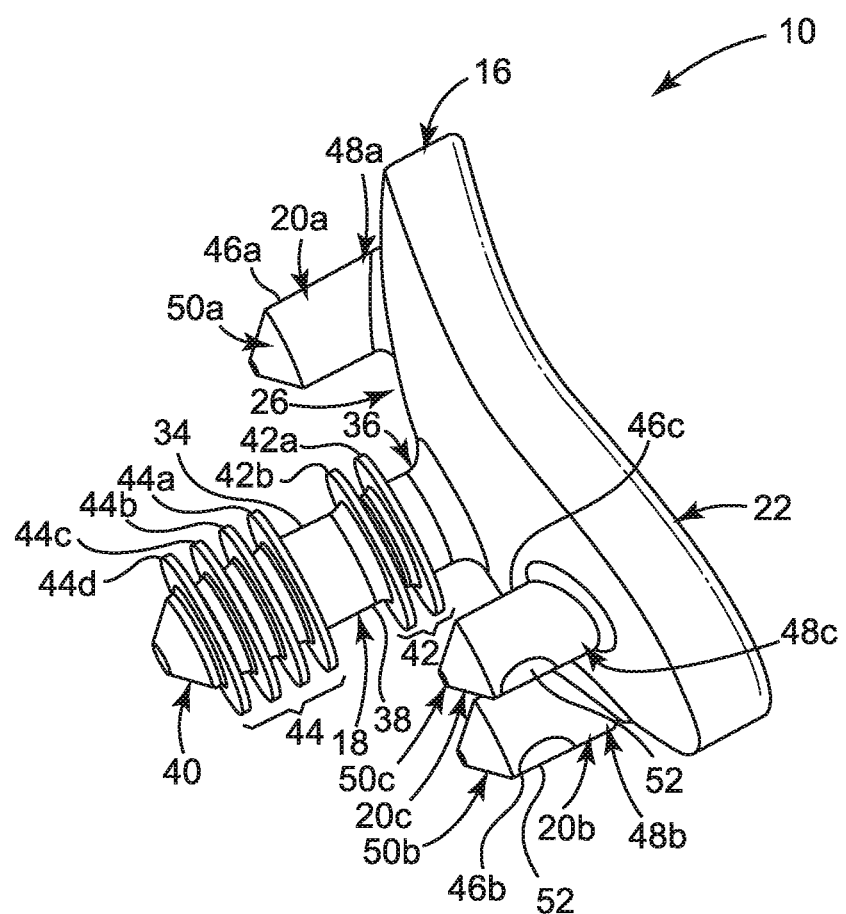
FIG. 2 is a perspective view of the glenoid component in accordance with an embodiment of the present invention.

Referring more particularly to FIG. 2, but still also in reference to FIG. 1, FIG. 2 shows a perspective view of the glenoid component 10, which functions to provide a replacement surface to articulate with the humeral component 14. The first articulating surface 22 of the head portion 16 is concave and configured to engage the humeral head 24 of the humeral component 14. The first articulating surface 22 is thus formed to accept at least a portion of the humeral head 24 within the concavity of the first articulating surface 22. The second surface 26 of the head portion 16 is preferably configured with the same shape as the glenoid 12 of the scapula S, which is usually convex.

In the illustrated embodiment, the anchor 18 extends substantially perpendicularly from the second surface 26 of the head portion 16 and secures the glenoid component 10 to the glenoid 12. In other embodiments, the anchor 18 may extend at various other angles relative to the second surface 26 of the head portion 16. The anchor 18 is preferably positioned substantially at the center of the second surface 26 of the head portion 16 and is in the form of a cylindrical shaft 34 having a proximal end 36, a middle section 38 and a distal end 40. The shaft 34 is attached to the head portion 16 at the proximal end 36 and tapers at the distal end 40 to facilitate insertion of the anchor 18 into the anchor hole 30 of the glenoid 12. In one embodiment, the distal end 40 of the anchor 18 includes a conical tip, or other shape that facilitates insertion into the glenoid 12, with or without the pre-drilled hole 30. Alternatively, the anchor 18 can have a tapered or stepped structure.

In the illustrated embodiment, the anchor 18 has a substantially consistent diameter. Distal fins 44 extend radially outward from the distal end 40 of the shaft 34 and proximal fins 42 extend radially outward from the proximal end 36 of the shaft 34. In the illustrated embodiment, the set of proximal fins 42 includes a first proximal fin 42a and a second proximal fin 42b. The set of distal fins 44 includes a first distal fin 44a, a second distal fin 44b, a third distal fin 44c and a fourth distal fin 44c.

In the illustrated embodiment, the sets of distal fins 44 and proximal fins 42 are spaced from each other by the middle section 38 of the shaft 34. In an alternate embodiment, the sets of proximal and distal fins 42, 44 extend the full length of the shaft 34 without being separated by the middle section 38.

Figure 3:
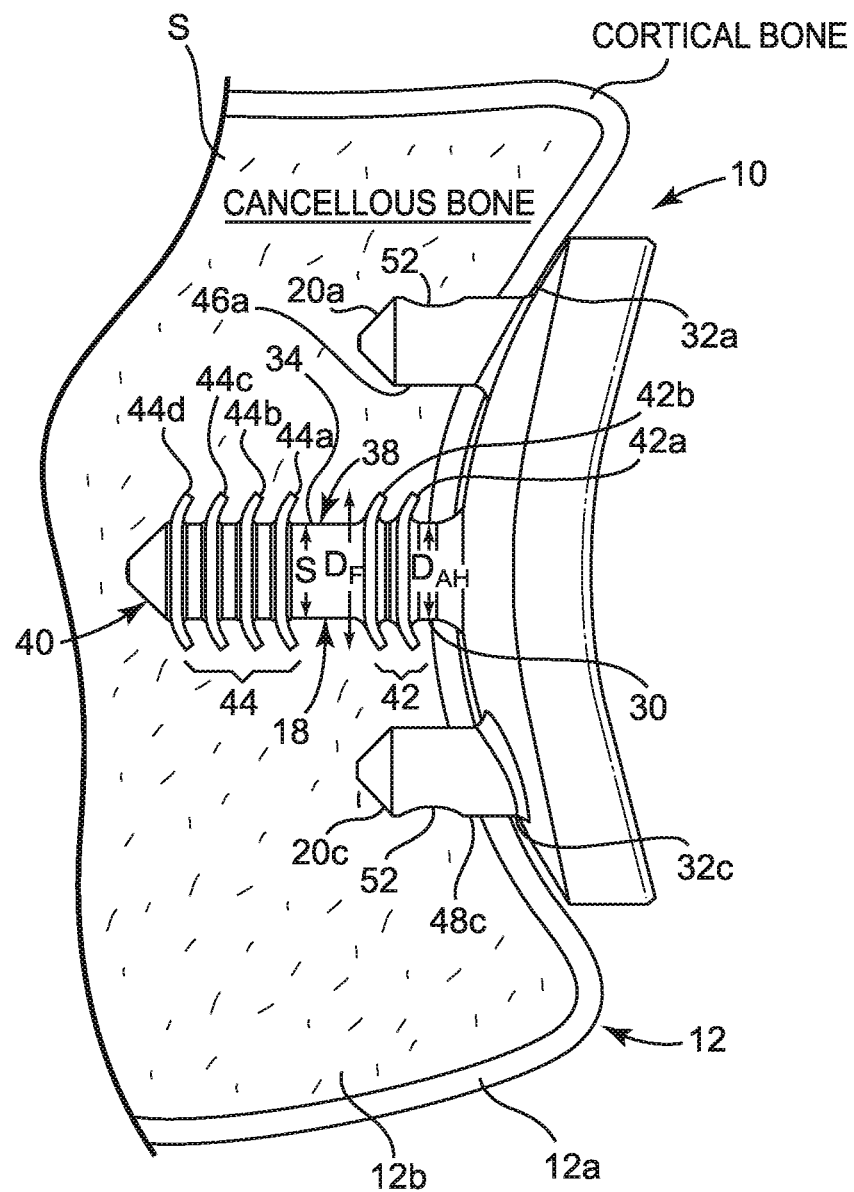
FIG. 3 is a side view of the glenoid component implanted in the glenoid in accordance with an embodiment of the present invention.

Both sets of proximal and distal fins 42, 44 are flexible and are configured to bend or deform when force is exerted against them. Deformation of the proximal and distal fins 42a, 42b, 44a, 44b, 44c, 44d can be plastic or elastic. For example, in one embodiment, the proximal and distal fins 42a, 42b, 44a, 44b, 44c, 44d deform plastically upon insertion into the glenoid 12 and retain a generally curved configuration, such as illustrated in FIG. 3. Alternatively, the proximal and distal fins 42a, 42b, 44a, 44b, 44c, 44d return to their un-deformed configuration after implantation.

In the illustrated embodiment, the proximal and distal fins 42a, 42b, 44a, 44b, 44c, 44d have substantially the same diameter. Consequently, the proximal and distal fins 42a, 42b, 44a, 44b, 44c, 44d are co-axial with each other and the outside edges are aligned. Although FIG. 2 depicts the set of proximal fins 42 as including two fins 42a, 42b and the set of distal fins 44 as including four fins 44a, 44b, 44c, 44d, the sets of proximal fins and distal fins 42, 44 may include any number of fins.

In one embodiment, the shaft 34 and the proximal and distal fins 42a, 42b, 44a, 44b, 44c, 44d of the anchor 18 are integrally formed with the head portion 16. For example, the glenoid component 10 can be molded as a single unitary structure or machined from a monolithic piece of material. In another embodiment, the shaft 34 and the proximal and distal fins 42a, 42b, 44a, 44b, 44c, 44d are separate components (See e.g., FIG. 10). In an alternate embodiment, the proximal and distal fins 42a, 42b, 44a, 44b, 44c, 44d are molded from a first material while the head portion 16 is molded from a second material. In this embodiment the first material preferably has a higher stiffness than the second material.

The glenoid component 10 of the present application can be manufactured from a variety of materials, such as for example polyethylene or ultra-high molecular weight polyethylene ("UHMWPE"), such as disclosed in U.S. Pat. No. 6,911,047, the disclosure of which is incorporated herein by reference.

The stabilizing pins 20 prevent the glenoid component 10 from moving relative to the glenoid 12 once the glenoid component 10 is implanted in the glenoid 12 and the scapula S. The stabilizing pins 20 preferably extend substantially perpendicularly from the second surface 26 of the head portion 16 and are positioned around the anchor 18. Each of the stabilizing pins 20a, 20b, 20c includes a body 46a, 46b, 46c (collectively referred to as "bodies 46"), respectively, having a proximal end 48a, 48b, 48c (collectively referred to as "proximal ends 48"), respectively, and a distal end 50a, 50b, 50c (collectively referred to as "distal ends 50"), respectively. Each of the bodies 46 of the stabilizing pins 20 is attached at its proximal end 48 to the head portion 16 of the glenoid component 10. The stabilizing pins 20 optionally include an indent or series of indents 52 to accept and lock in bone cement, maintaining the stabilizing pins 20 in position.

The stabilizing pins 20 are preferably shorter than the anchor 18 and in one embodiment extend only slightly past the set of proximal fins 42 of the anchor 18. Similar to the distal end 40 of the anchor 18, the distal ends 50 of the stabilizing pins 20 are also tapered to facilitate insertion of the stabilizing pins 20 into the stabilizing holes 32 of the glenoid 12. In one embodiment, the distal ends 50 of the stabilizing pins 20 have a conical tip, or other shape that facilitates insertion into the glenoid 12, with or without pre-drilled hole 32.

The stabilizing pins 20 may be arranged in any configuration on the second side 26 of the head portion 16 around the anchor 18. In one embodiment, the stabilizing pins 20 are positioned such that the first stabilizing pin 20a is positioned farther from the anchor 18 than the second and third stabilizing pins 20b, 20c. In another embodiment, the stabilizing pins 20 are positioned around the anchor 18 along a periphery of the head portion 16 substantially equidistant from the anchor 18 and each adjacent stabilizing pin 20a, 20b, 20c. Although FIG. 2 depicts the glenoid component 10 as including three stabilizing pins 20, the glenoid component 10 may include any number of stabilizing pins, including zero, without departing from the intended scope of the present invention. When the glenoid component 10 does not include any stabilizing pins, any means for preventing rotation of the glenoid component 10 relative to the glenoid 12 may be used. For example, the glenoid 12 may be milled in an oval shape and the glenoid component 10 may be key implanted into the bone.

FIG. 3 shows a side view of the glenoid component 10 implanted through the glenoid 12 and into the scapula S. In practice, to attach the glenoid component 10 to the glenoid 12, the anchor hole 30 and the plurality of stabilizing holes 32 are preferably first drilled or otherwise formed in the glenoid 12. The anchor hole 30 is preferably sized to have a diameter $D_{AH}$ slightly larger than a diameter $D_S$ of the shaft 34 of the anchor 18 but smaller than a diameter $D_F$ of the distal and proximal fins 42a, 42b, 44a, 44b, 44c, 44d of the anchor 18. Because the proximal and distal fins 42a, 42b, 44a, 44b, 44c, 44d are flexible, even though the diameters $D_F$ of the proximal and distal fins 42a, 42b, 44a, 44b, 44c, 44d are larger than the diameter $D_{AH}$ of the anchor hole 30, the proximal and distal fins 42a, 42b, 44a, 44b, 44c, 44d can pass through the anchor hole 30 by exerting an extra amount of force on the glenoid component 10 and causing the proximal and distal fins 42a, 42b, 44a, 44b, 44c, 44d to deform.

The stabilizing holes 32 are drilled around the anchor hole 30 and are sized to accept the stabilizing pins 20. The stabilizing pins 20 may be press fit or interference fit into the stabilizing holes 32. Optionally, bone cement may also be utilized to help maintain the stabilizing pins 20 within the stabilizing holes 32. If it is desired to use bone cement to aid in securing the glenoid component 10 to the glenoid 12, the bone cement can be applied at the indents 52 of the bodies 46 of the stabilizing pins 20 to increase the area of contact between the stabilizing pins 20 and the bone cement in order to increase the bond to secure the stabilizing pins 20 within the stabilizing holes 32.

The anchor hole 30 and the stabilizing holes 32 are drilled such that when the glenoid component 10 is positioned with respect to the glenoid 12, the anchor 18 is aligned with the anchor hole 30 and the stabilizing pins 20 are aligned with the stabilizing holes 32. In one embodiment, a drill guide or pattern may be used to properly position and align the anchor hole 30 and the stabilizing holes 32 in the glenoid 12 to correspond with the positions and alignments of the anchor 18 and stabilizing pins 20 of the glenoid component 10, respectively.

After the anchor hole 30 and the stabilizing holes 32 have been formed in the glenoid 12 and the scapula S, the glenoid component 10 is positioned in front of the glenoid 12 such that the anchor 18 and stabilizing pins 20 of the glenoid component 10 are aligned with the anchor hole 30 and the stabilizing holes 32, respectively, of the glenoid 12. As the glenoid component 10 is directed towards the glenoid surface 12, the conical tip at the distal end 40 of the shaft 34 of the glenoid component 10 first enters the anchor hole 30. When the set of distal fins 44 contact the cortical bone 12a, each of the distal fins 44a, 44b, 44c, 44d deforms sequentially in order to pass through the anchor hole 30. Once the set of distal fins 44 are advanced past the cortical bone 12a, they engage with the softer cancellous bone 12b.

Figure 10:
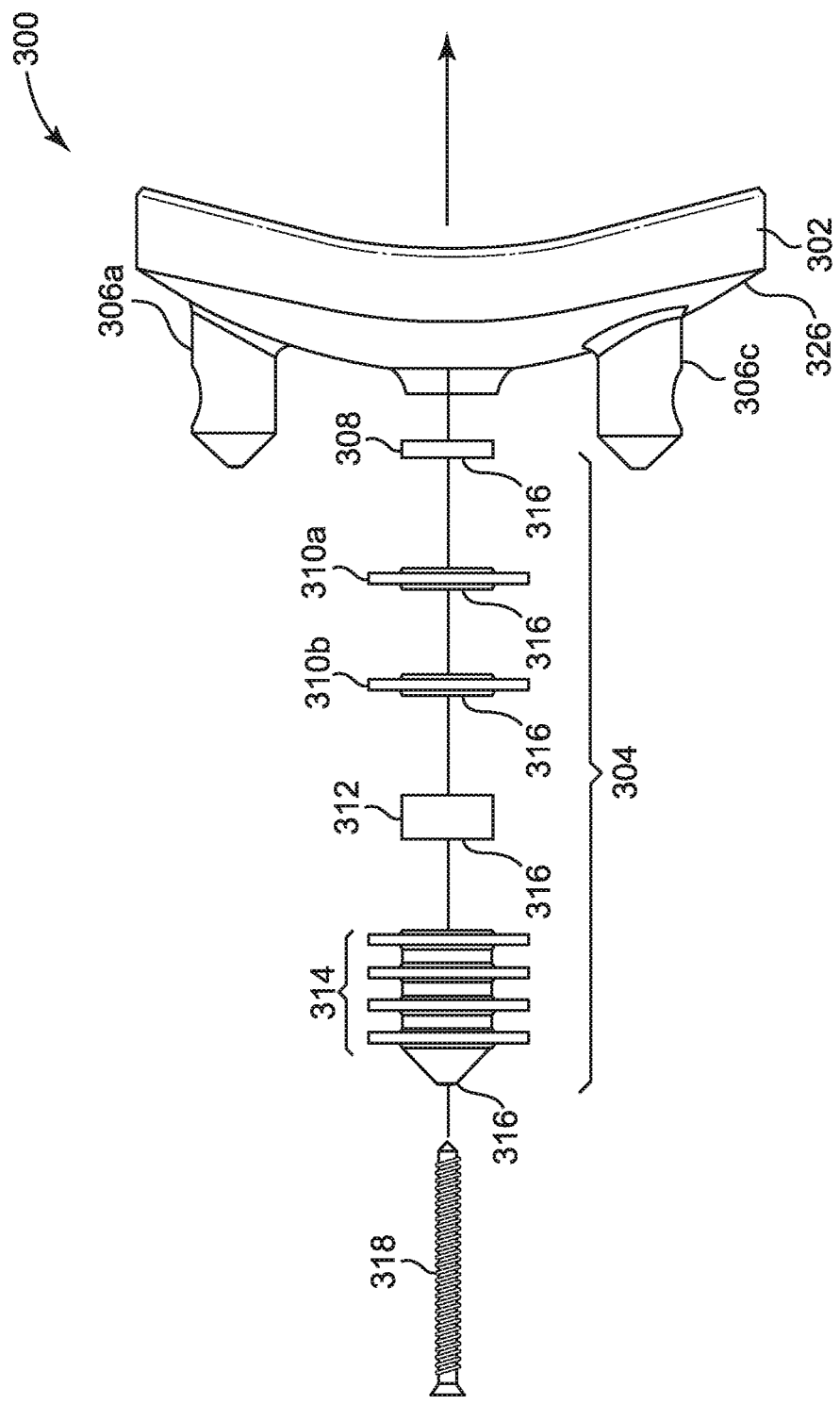
FIG. 10 is an exploded side view an alternative glenoid component in accordance with an embodiment of the present invention.

The distance "d" between the first proximal fin 42a and the second surface 26 of the head portion 16 corresponds generally to the thickness of the cortical bone 12a. The distance "d" is generally between about 1 to about 4 millimeters, and preferably between about 2 to about 3 millimeters. In the embodiment of FIG. 10, the distance "d" is adjustable by substituting a different spacer 306.

The proximal fins 42a, 42b provide resistance against the smaller diameter $D_{AH}$ of the anchor hole 30 so enough force must be exerted in order to engage the proximal fins 42a, 42b with the cortical bone 12a. Once past the anchor hole 30, the set of proximal fins 42 pass through the cortical bone 12a and into the cancellous bone 12b of the scapula S. In one embodiment, the first proximal fin 42a is positioned in the cortical bone 12a and the second proximal fin 42b is positioned adjacent to the cortical bone 12a.

In order to fully insert the anchor 18 through the anchor hole 30, the stabilizing pins 20 must be aligned with stabilizing holes 32 such that the stabilizing pins 20 engage with respective stabilizing holes 32. Thus, as the anchor 18 is advanced into the anchor hole 30, the stabilizing pins 20 are simultaneously advanced into the stabilizing holes 32. Because the stabilizing pins 20 have a substantially consistent diameter and the stabilizing holes 32 are sized to accept the stabilizing pins 20, extra force is not required to advance the stabilizing pins 20 into the scapula S. The glenoid component 10 is advanced into the scapula S until the second surface 26 of the head portion 16 abuts the glenoid 12 and the anchor 18 and stabilizing pins 20 are fully inserted into the scapula S. When the anchor 18 is positioned through the anchor hole 30 and the stabilizing pins 20 are positioned through the stabilizing holes 32, the stabilizing pins 20 prevent rotation or movement of the glenoid component 10 relative to the glenoid 12.

When the sets of proximal and distal fins 42, 44 of the anchor 18 are positioned within the scapula S, the proximal and distal fins 42a, 42b, 44a, 44b, 44c, 44d are bent towards the glenoid 12, securing the glenoid component 10 to the scapula S. The anchor 18 of the glenoid component 10 is positioned in the scapula S such that the sets of distal and proximal fins 42, 44 are embedded in the cancellous bone 12b, which has low density and strength and fills the inner cavity of the scapula S. Because the set of proximal fins 42 is located proximate the second surface 26 of the head portion 16, the set of proximal fins 42 is located adjacent and proximate the cortical bone 12a, which is dense and forms the surface of the scapula S. The first proximal fin 42a abuts the cortical bone 12a, providing resistance to prevent the set of proximal fins 42 from passing through the anchor hole 30 and removing the anchor 18 from the scapula S. In addition, in the deformed state, the proximal fins 42a, 42b also function to stabilize the shaft 34 and prevent the shaft 34 from bending when side loaded. Because the set of proximal fins 42 substantially continuously abuts against the cortical bone 12a, the glenoid component 10 provides increased resistance to removal from the scapula S compared to a glenoid component that does not include a set of proximal fins.

In addition, over time, as the glenoid component 10 remains within the scapula S, tissue will grow into the spaces between the fins 42a, 42b, 44a, 44b, 44c, 44d and provide further resistance to pulling out the anchor 18 from the anchor hole 30. The combination of the configuration of the sets of proximal and distal fins 42, 44 within the scapula S and the tissue that grows around the fins 42a, 42b, 44a, 44b, 44c, 44d eliminates or reduces the need to use bone cement or other adhesive means to secure the glenoid component 10 to the glenoid 12. Likewise, the indents 52 in the bodies 46 of the stabilizing pins 20 also provide an area for tissue to grow, further increasing the force required to remove the glenoid component 10 from the scapula S.

Referring back to FIG. 1, once the glenoid component 10 is fixed to the glenoid 12 and the scapula S, the first articulating surface 22 of the head portion 16 of the glenoid component 10 acts as an articulating or bearing surface for engaging the humeral head 24 of the humeral component 14. The glenoid component 10 thus functions as a replacement for the natural glenoid of the scapula S, allowing the glenoid component 10, the glenoid 12 and the humeral component 14 to interact similarly to a natural shoulder socket.

Figure 4:
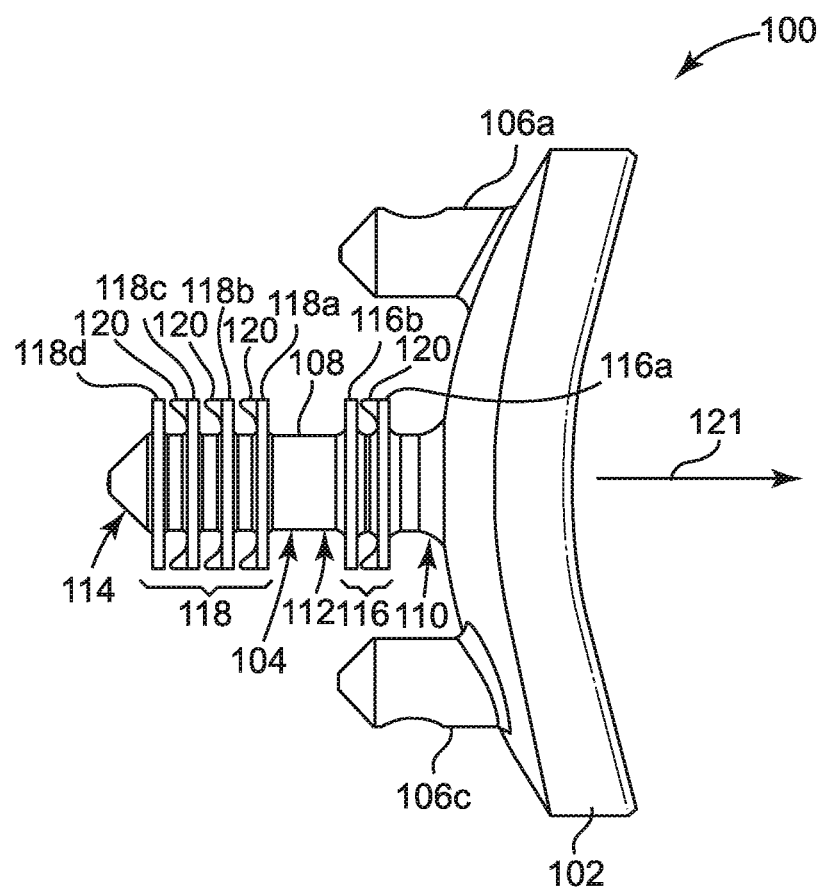
FIG. 4 is a side view of an alternative glenoid component in accordance with an embodiment of the present invention.

FIG. 4 shows a side view of an alternative glenoid component 100. The glenoid component 100 functions substantially similarly to the glenoid component 10 of FIGS. 1 and 2 and includes a head portion 102, an anchor 104 and a plurality of stabilizing pins 106a, 106b (not shown), 106c. The anchor 104 includes a shaft 108 having a proximal end 110, a middle section 112 and a distal end 114. A set of proximal fins 116 extends radially from the proximal end 110 of the shaft 108 and a set of distal fins 118 extends radially from the distal end 114 of the shaft 108. The sets of proximal and distal fins 116, 118 are optionally separated by the middle section 112 of the shaft 108.

The anchor 104 of the glenoid component 100 is substantially similar to the anchor 18 of the glenoid component 10 of FIGS. 1 and 2 except that each of the first proximal fin 116a and the first, second and third distal fins 118a, 118b and 118c includes a rib feature 120 to create preferential deformation of the fins 116a, 118a, 118b and 118c. The rib features 120 function to transfer load between the proximal fins 116a, 116b, and between the distal fins 118a, 118b, 118c, 118d, to reduce fin deformation in response to a removal force 121. For example, when the glenoid component 10 is being pulled away from the glenoid 12 (FIG. 1), the rib feature 120 of the first proximal distal fin 116a abuts the second proximal fin 116b, reducing deformation arising from the removal force 121. Likewise, the rib feature 120 of the first distal fin 118a abuts the second distal fin 118b, the rib feature 120 of the second distal fin 118b abuts the third distal fin 118c and the rib feature 120 of the third distal fin 118c abuts the fourth proximal fin 118d, reducing deformation of the respective first, second and third distal fins 118a, 118b, 118c in response to the removal force 121. The fins 116a, 118a, 118b, 118c are substantially uni-directionally deformable. As used herein, "uni-directionally deformable" or "uni-directional deformation" refer to a structure that deforms in a first direction, but resists deformation in an opposite second direction.

Figure 5:
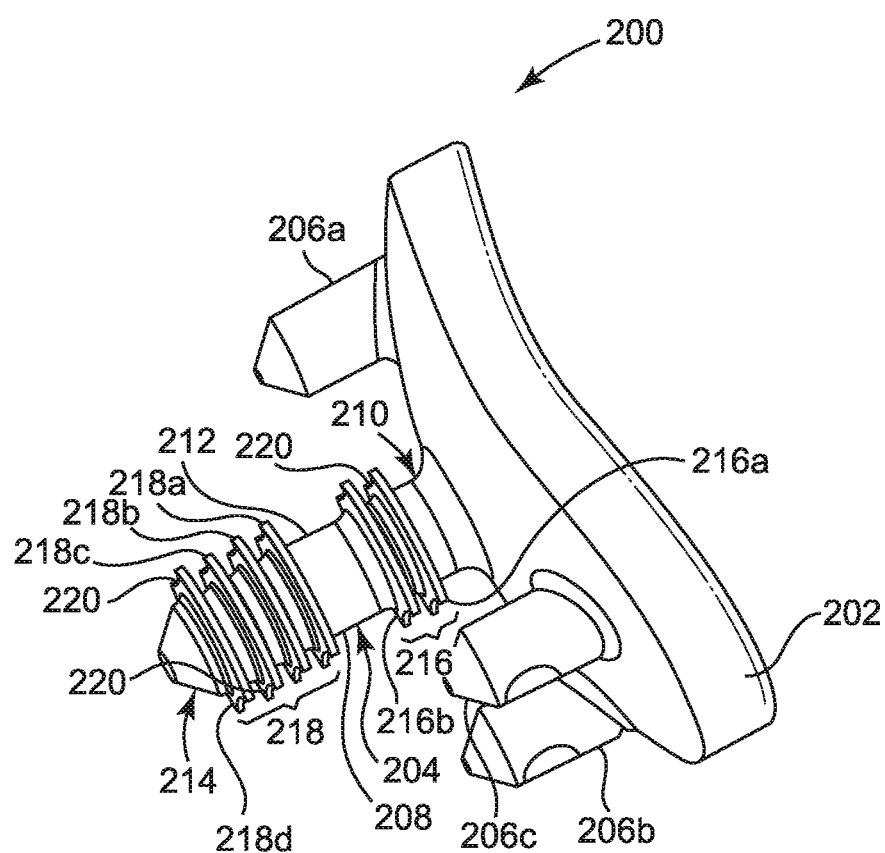
FIG. 5 is a perspective view of an alternative glenoid component in accordance with an embodiment of the present invention.

FIG. 5 shows a perspective view of an alternative glenoid component 200. The glenoid component 200 functions substantially similarly to the glenoid component 10 of FIGS. 1 and 2 and includes a head portion 202, an anchor 204 and a plurality of stabilizing pins 206a, 206b, 206c. The anchor 204 includes a shaft 208 having a proximal end 210, a middle section 212 and a distal end 214. A set of proximal fins 216 extends radially from the proximal end 210 of the shaft 208 and a set of distal fins 218 extends radially from the distal end 214 of the shaft 208. The proximal and distal fins 216, 218 are optionally separated by the middle section 212 of the shaft 208.

The anchor 204 of the glenoid component 200 is substantially similar to the anchor 18 of the glenoid component 10 of FIGS. 1 and 2 except that each of the proximal and distal fins 216a, 216b, 218a, 218b, 218c, 218d includes one or more cut-outs 220. As the glenoid component 10 is pushed into the scapula S, additional force is needed to pass the proximal and distal fins 216a, 216b, 218a, 218b, 218c, 218d through the anchor hole 30. By reducing the surface area of the proximal and distal fins 216a, 216b, 218a, 218b, 218c, 218d, the amount of force required to insert the glenoid component 10 is also reduced.

In one embodiment, radial cut-outs 220 are machined through all of the proximal and distal fins 216a, 216b, 218a, 218b, 218c, 218d in order to reduce the surface area. Although FIG. 5 depicts the cut-outs 220 as being positioned substantially symmetrically around the anchor 204, the cut-outs 220 may be positioned anywhere around the anchor 204 without departing from the intended scope of the invention. In addition, there may be any number of cut-outs 220 machined from the proximal and distal fins 216a, 216b, 218a, 218b, 218c, 218d.

Figure 6:
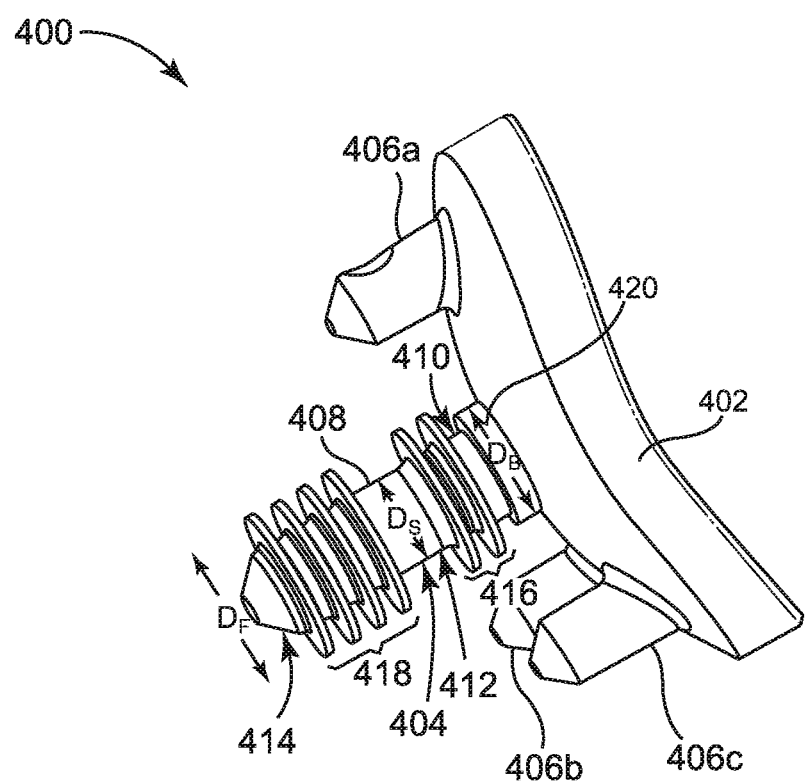
FIG. 6 is a perspective view of an alternative glenoid component in accordance with an embodiment of the present invention.

FIG. 6 shows a perspective view of an alternative glenoid component 400. The glenoid component 400 functions substantially similarly to the glenoid component 10 of FIGS. 1 and 2 and includes a head portion 402, an anchor 404 and a plurality of stabilizing pins 406a, 406b, 406c. The anchor 404 includes a shaft 408 having a proximal end 410, a middle section 412 and a distal end 414. A set of proximal fins 416 extends radially from the proximal end 410 of the shaft 408 and a set of distal fins 418 extends radially from the distal end 414 of the shaft 408. The sets of distal and proximal fins 416, 418 are optionally separated by the middle section 412 of the shaft 108.

The anchor 404 of the glenoid component 400 is substantially similar to the anchor 18 of the glenoid component 10 of FIGS. 1 and 2 except that the proximal end 410 of the shaft 408 of the anchor 404 includes a stabilizing boss 420. The stabilizing boss 420 has a diameter $D_B$ that is larger than the diameter $D_S$ of the shaft 408 but smaller than the diameters $D_F$ of the sets of proximal and distal fins 416, 418. The stabilizing boss 420 functions to aid in stabilizing the shaft 408 in a radial load condition. In one embodiment, the stabilizing boss 420 has a diameter substantially equal to the diameter of the anchor hole 30 $D_{AH}$ (FIG. 3) to help prevent the shaft 408 from bending when side loaded.

Figure 7A:
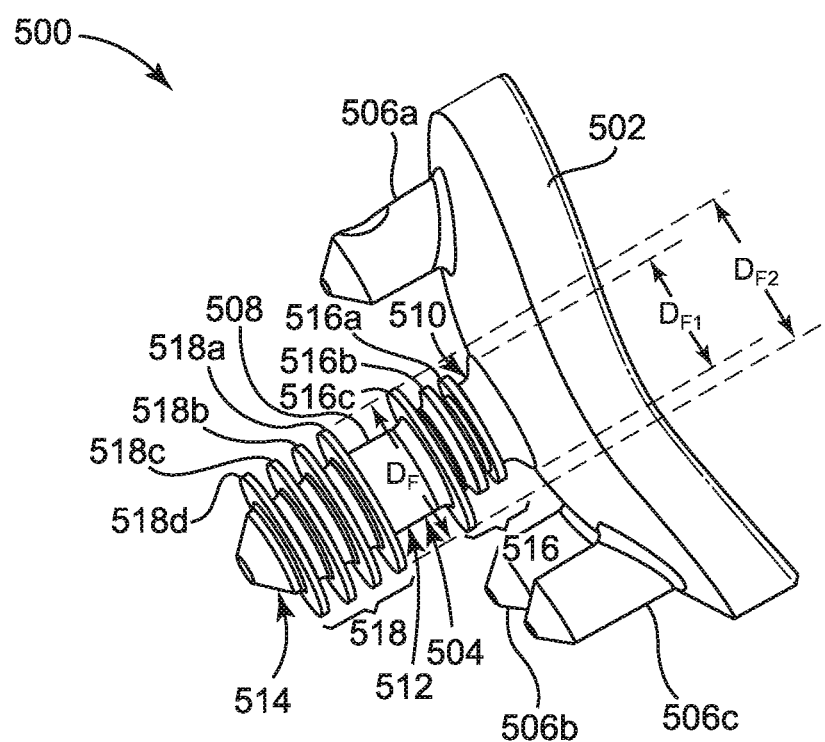
FIG. 7A is a perspective view of an alternative glenoid component in accordance with an embodiment of the present invention.
Figure 7B:
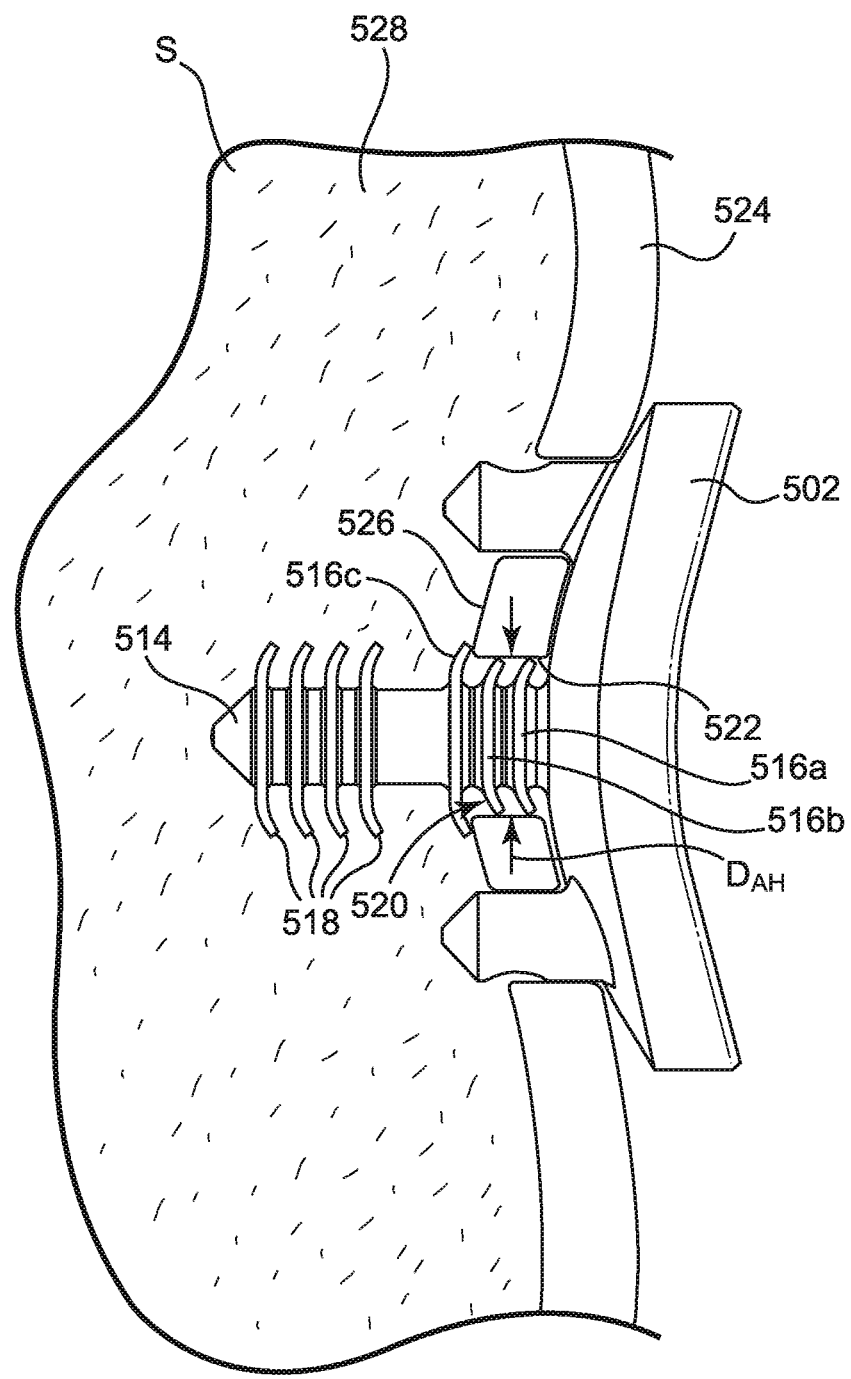
FIG. 7B is a side view of the alternative glenoid component of FIG. 7A in accordance with an embodiment of the present invention.

FIGS. 7A and 7B show a perspective view and a side view, respectively, of an alternative glenoid component 500. The glenoid component 500 functions substantially similarly to the glenoid component 10 of FIGS. 1 and 2 and includes a head portion 502, an anchor 504 and a plurality of stabilizing pins 506a, 506b, 506c. The anchor 504 includes a shaft 508 having a proximal end 510, a middle section 512 and a distal end 514. A set of proximal fins 516 extends radially from the proximal end 510 of the shaft 508 and a set of distal fins 518 extends radially from the distal end 514 of the shaft 508. The proximal and distal fins 516, 518 are optionally separated by the middle section 512 of the shaft 508.

The anchor 504 of the glenoid component 500 is substantially similar to the anchor 18 of the glenoid component 10 of FIGS. 1 and 2 except that the diameters of the proximal fins 516a, 516b, 516c are not the same. In the illustrated embodiment, the first and second proximal fins 516b, 516b have a smaller diameter than the diameter $D_F$ of the third proximal fin 516c. The smaller diameters of the first and second proximal fins 516a, 516b function to stabilize the shaft 508 of the anchor 504 and to prevent the shaft 508 from bending from side loading. In one embodiment, the diameters of the first and second proximal fins 516a, 516b are substantially equal to the diameter of the anchor hole 30 $D_{AH}$. Although FIGS. 7A and 7B depict only the first and second proximal fins 516a, 516b as having a different diameter than the rest of the proximal and distal fins 516c, 518a, 518b, 518c, 518d, any of the proximal and/or distal fins 516a, 516b, 516c, 518a, 518b, 518c, 518d may have varying diameters.

Figure 8:
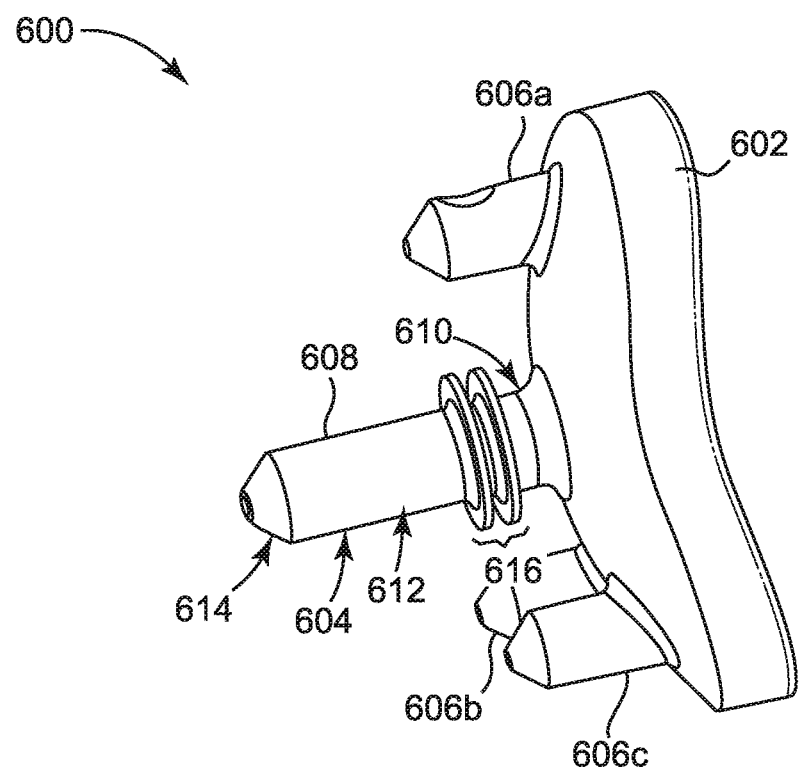
FIG. 8 is a perspective view of an alternative glenoid component in accordance with an embodiment of the present invention.

FIG. 8 shows a perspective view of an alternative glenoid component 600. The glenoid component 600 functions substantially similarly to the glenoid component 10 of FIGS. 1 and 2 and includes a head portion 602, an anchor 604 and a plurality of stabilizing pins 606a, 606b, 606c. The anchor 604 includes a shaft 608 having a proximal end 610, a middle section 612 and a distal end 614. A set of proximal fins 616 extends radially from the proximal end 610 of the shaft 608.

The anchor 604 of the glenoid component 600 is substantially similar to the anchor 18 of the glenoid component 10 of FIGS. 1 and 2 except that the anchor 604 does not include a set of distal fins. Thus, the middle section 612 and the distal end 614 of the shaft 608 are smooth with no radial extensions. The embodiment shown in FIG. 8 illustrates that distal fins are not required to fixate the glenoid component 600 to the glenoid 12 (FIG. 1). When the anchor 604 does not include any distal fins, initial fixation can still be achieved using only the set of proximal fins 616.

Figure 9A:
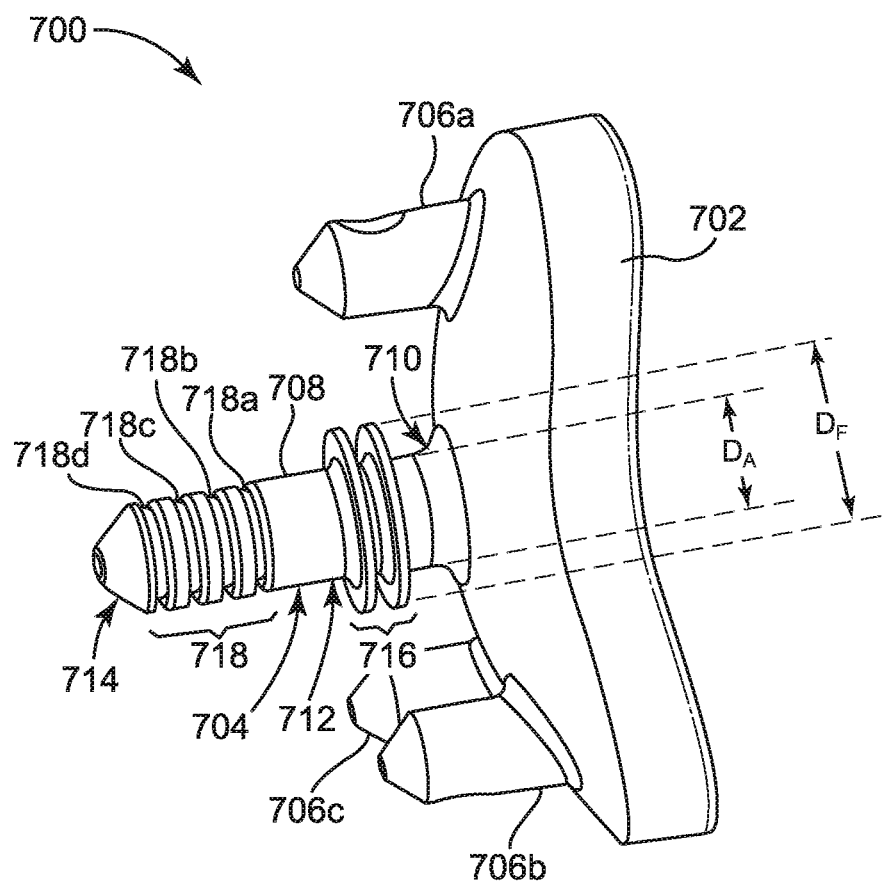
FIG. 9A is a perspective view of an alternative glenoid component in accordance with an embodiment of the present invention.

FIG. 9A shows a perspective view of an alternative glenoid component 700. The glenoid component 700 functions substantially similarly to the glenoid component 10 of FIGS. 1 and 2 and includes a head portion 702, an anchor 704 and a plurality of stabilizing pins 706a, 706b, 706c. The anchor 704 has a diameter $D_A$ and includes a shaft 708 having a proximal end 710, a middle section 712 and a distal end 714. A set of proximal fins 716 extends radially from the proximal end 710 of the shaft 708 and has a diameter $D_F$.

The anchor 704 of the glenoid component 700 is substantially similar to the anchor 18 of the glenoid component 10 of FIGS. 1 and 2 except that rather than having a set of distal fins extending radially from the distal end 714 of the shaft 708, the distal end 714 includes a plurality of grooves 718a, 718b, 718c, 718d (collectively referred to as "grooves 718") machined into the shaft 708. The grooves 718 may be machined into the distal end 714 of the shaft 708 by any means known in the art. In one embodiment, the grooves 718 are machined into the shaft 708 by step drilling. Similar to the glenoid component 600 shown in FIG. 8, initial fixation of the anchor 704 of the glenoid component 700 can still be achieved using just the set of proximal fins 716. After the initial fixation, long term fixation is achieved through bone in-growth into the grooves 718. Although FIG. 9 depicts the distal end 714 of the shaft 708 as including four grooves 718, the distal end 714 of the shaft 708 may include any number of grooves.

Figure 9B:
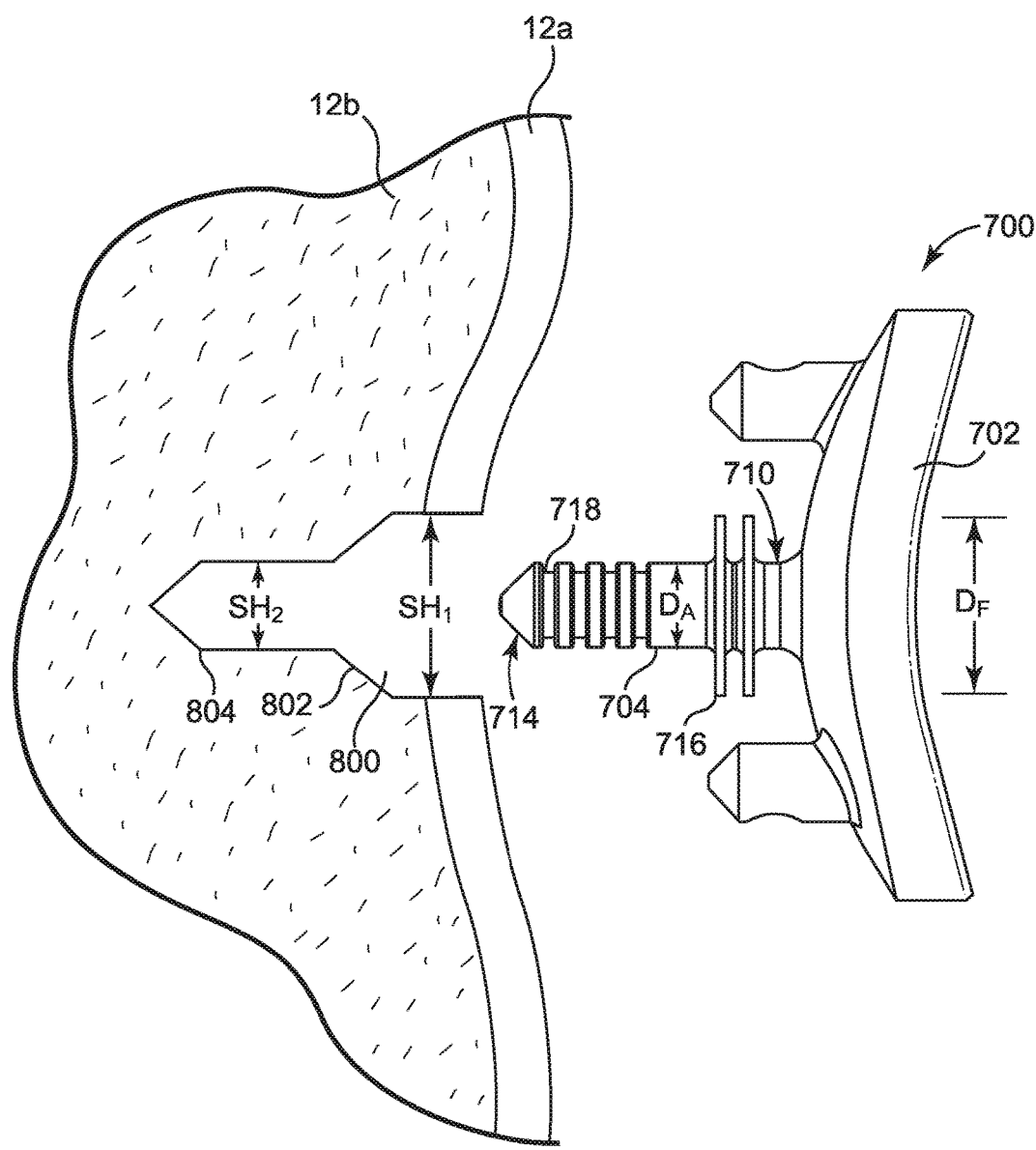
FIG. 9B is a side view of a stepped hole configuration in accordance with an embodiment of the present invention.
Figure 9C:
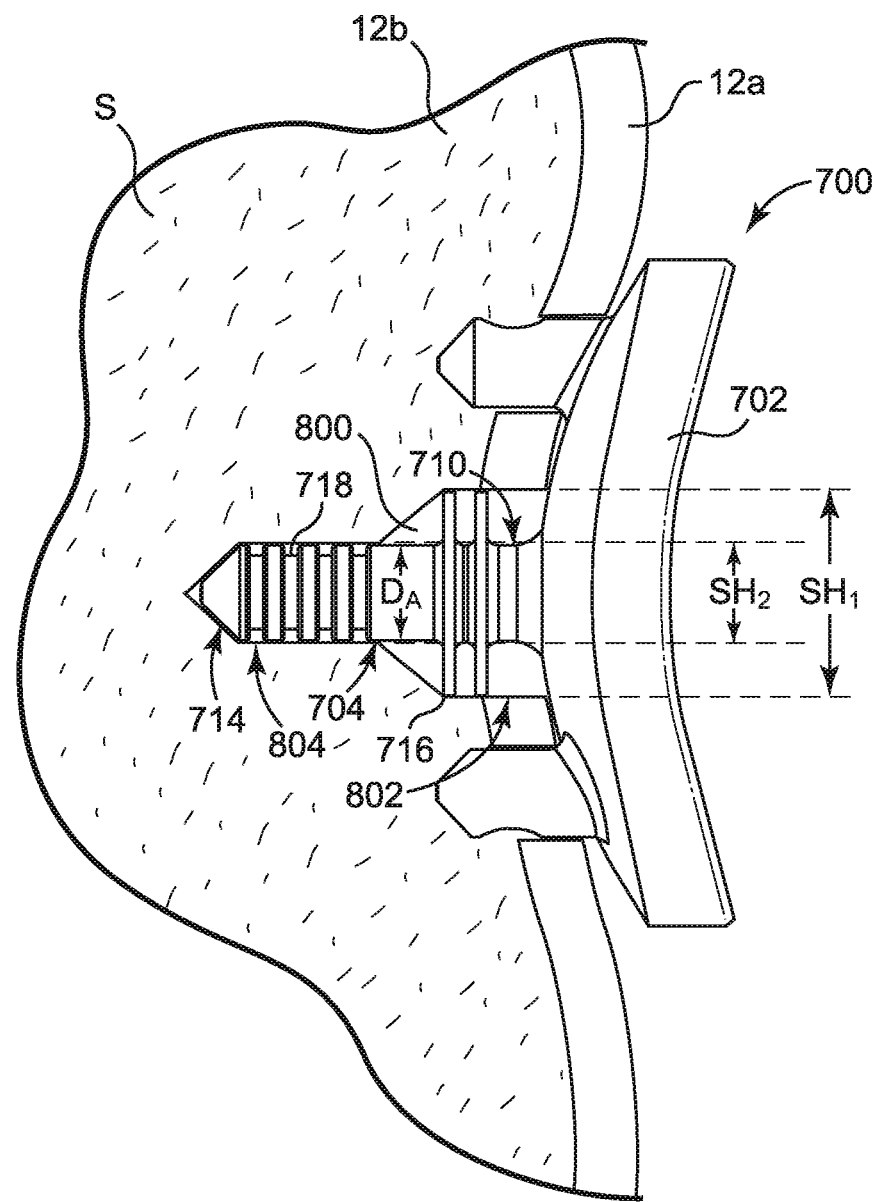
FIG. 9C is a side view of the alternative glenoid component of FIG. 9A positioned within the stepped hole configuration of FIG. 9B in accordance with an embodiment of the present invention.

FIG. 9B shows a side view of a stepped hole configuration 800 created through the cortical bone 12a and within the cancellous bone 12b. FIG. 9C shows a side view of the anchor 704 of the glenoid component 700 positioned within the stepped hole configuration 800. The stepped hole 800 is sized to receive the anchor 704 of the glenoid component 700 and initially reduce the amount of force required to insert the anchor 704 of the glenoid component 700 into the scapula S. The stepped hole 800 includes a proximal portion 802 having a first diameter $SH_1$ and a distal portion 804 having a second diameter $SH_2$ bone 12b. The proximal portion 802 is located through the cortical bone 12a and the cancellous bone 12b and the distal portion 804 is located within the cancellous bone 12b. The first diameter $SH_1$ is greater than the second diameter $SH_2$ and slightly smaller than the diameter $D_F$ (FIG. 9B) of the set of proximal fins 716. The second diameter $SH_2$ is substantially the same size as the diameter $D_A$ of the anchor 704, allowing easily insertion of the distal end 714 of the anchor into the stepped hole 800. Because the diameter $D_F$ of the set of proximal fins 716 is greater than the first diameter $SH_1$ of the stepped hole 800, as the proximal end 710 of the anchor 704 is inserted into the stepped hole 800, there is "lock-up" of the set of proximal fins 716 under the cortical bone 12a.

Once the anchor 704 is positioned in the stepped hole, the relative sizes of the second diameter $SH_2$ of the stepped hole 800 and the anchor $D_A$ allows for bone ingrowth into the recessed grooves 718 at the distal end 714 of the shaft 708. Although the stepped hole 800 is discussed with relation to glenoid component 700, the stepped hole 800 may be used with other glenoid components in which the proximal end of the anchor has a greater diameter than the distal end of the anchor. For example, the stepped hole configuration 800 may also be used with the glenoid component 600 shown in FIG. 8. In one embodiment, the step hole 800 is formed using a step drill. FIG. 10 shows an exploded side view of an alternative glenoid component 300. In order to accommodate patients of various shapes and sizes, the glenoid component 300 may have a modular design. The glenoid component 300 functions substantially similarly to the glenoid component 10 of FIGS. 1 and 2 and includes a head portion 302, an anchor portion 304 and a plurality of stabilizing pins 306a, 306b (not shown), 306c. The head portion 302 is preferably a single piece of material, while the anchor portion 304 is formed of a plurality of modular pieces.

In the embodiment shown in FIG. 10, the anchor portion 304 includes a first spacer 308, a first proximal fin 310a, a second proximal fin 310b, a second spacer 312 and a set of distal fins 314. The first spacer 308 sets an offset between a second surface 326 of the head portion 302 and the first proximal fin 310a corresponding generally to a thickness of the cortical bone 12a (FIG. 3).

Each of the modular pieces 308, 310a, 310b, 312, 314 of the anchor portion 304 includes a bore 316 running through the center of the pieces 308, 310a, 310b, 312, 314 such that they can be maintained together and fixed to the head portion 302 by a screw 318. Although FIG. 10 shows the glenoid component 300 as including the modular pieces 308, 310a, 310b, 312, 314, the glenoid component 300 may include any number of modular pieces without departing from the intended scope of the present invention. For example, the glenoid component 300 may include additional spacers to accommodate a patient with larger proportions or may include only one spacer to accommodate a patient with smaller proportions. Various spacers may also be provided having varying thicknesses. In another embodiment, additional fins may be included adjacent the set of distal fins 314 or one of the proximal fins 310a, 310b.

The embodiment of FIG. 10 is particularly well suited for building the glenoid component 300 from multiple materials. For example, the head portion 302 can be made from a first material and one or more of the other pieces 308, 310a, 310b, 312, 314 can be made from one or more second materials. Forming the pieces 308, 310a, 310b, 312, 314 separately also facilitates formation of various structures to achieve uni-lateral deformation.

While each of the embodiments of FIGS. 4 through 10 are discussed as separate, alternative glenoid components to the glenoid component 10 shown in FIGS. 1-3, the individual structural features of each of the embodiments may be incorporated into any glenoid component. For example, the glenoid component 700 (FIG. 9) having the distal grooves 718 may also include the stabilizing boss 420 (FIG. 6) or the proximal fins 516a and 516b having decreased diameters (FIG. 7) for increased stability.

EXAMPLES

The present invention is more particularly described in the following examples that are intended as illustrations only, since numerous modifications and variations within the scope of the present invention will be apparent to those skilled in the art.

Example 1

Insertion

Figure 11:
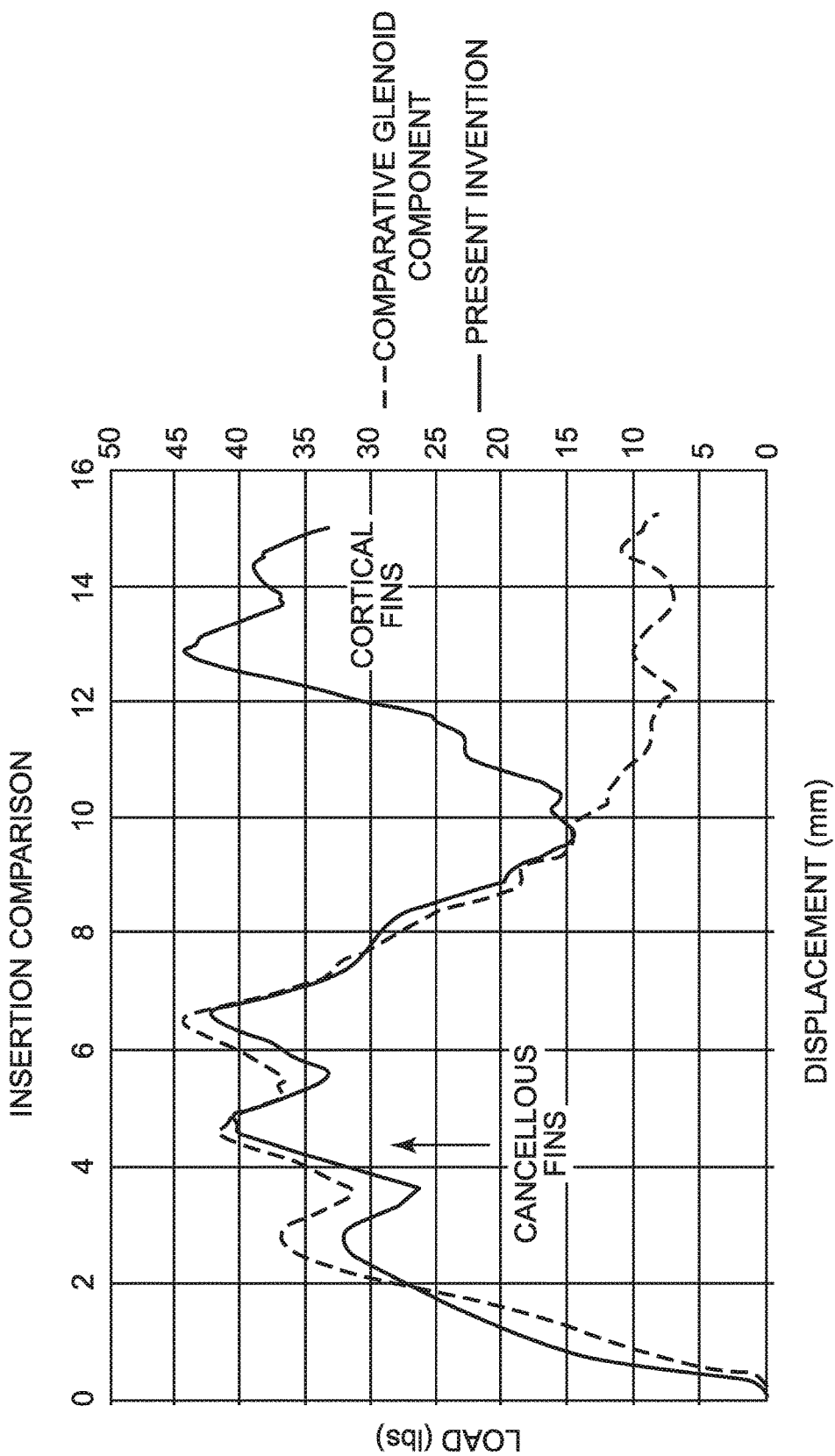
FIG. 11 is a graph of load versus displacement during insertion of the glenoid component in accordance with an embodiment of the present invention.

FIG. 11 illustrates the load versus displacement of a glenoid component of the present invention and the load versus displacement of a comparative glenoid component during insertion into a foam structure designed to exhibit similar density properties of a scapula. The foam structure included an anchor hole for accepting an anchor of the glenoid component of the present invention and an anchor of the comparative glenoid component.

The glenoid component of the present invention included an anchor having a set of four distal fins extending from a distal end of the anchor and a set of two proximal fins extending from a proximal end of the anchor. The set of distal fins and the set of proximal fins are separated by a middle section of the anchor, such as illustrated in FIG. 2. The set of proximal fins were offset from a rear surface of the head portion by about 2.5 millimeters.

The comparative glenoid component was substantially similar to the glenoid component of the present invention except that the comparative glenoid component did not include a set of proximal fins positioned to engage with the cortical bone. The comparative glenoid component included only a set of four distal fins.

As can be seen in FIG. 11, the force required to advance the distal end of the glenoid component of the present invention and the distal end of the comparative glenoid component into the foam structure was comparable. Initially, the distal fins on both glenoid components contacted the anchor hole of the foam structure. To advance each of the distal fins through the anchor hole, the amount of force that was applied to the glenoid component increased, creating a first spike, a second spike and a third spike corresponding to the location of the first, second, and third distal fins along the distal end of the anchor.

As the glenoid component of the present invention was advanced further into the foam structure, however, the amount of force required to advance the anchor through the anchor hole increased in response to the first and second proximal fins engaging the anchor hole. The amount of force required to advance the proximal fins into the foam structure increased sharply as the first proximal fin and then the second proximal fin contacted the anchor hole, spiking to a required load of about 44.5 pounds and 39.5 pounds, respectively.

By contrast, the comparative glenoid component did not require additional force to advance the proximal end of the anchor into the anchor hole. Rather, the amount of force required to advance the comparative glenoid component into the foam structure steadily decreased to about 10 or about 11 pounds. On average, the glenoid component of the present invention required about 75% more force to insert the proximal end of the anchor through the anchor hole than required to insert the proximal end of the anchor of the comparative glenoid component through the anchor hole.

Example 2

Removal

Figure 12:
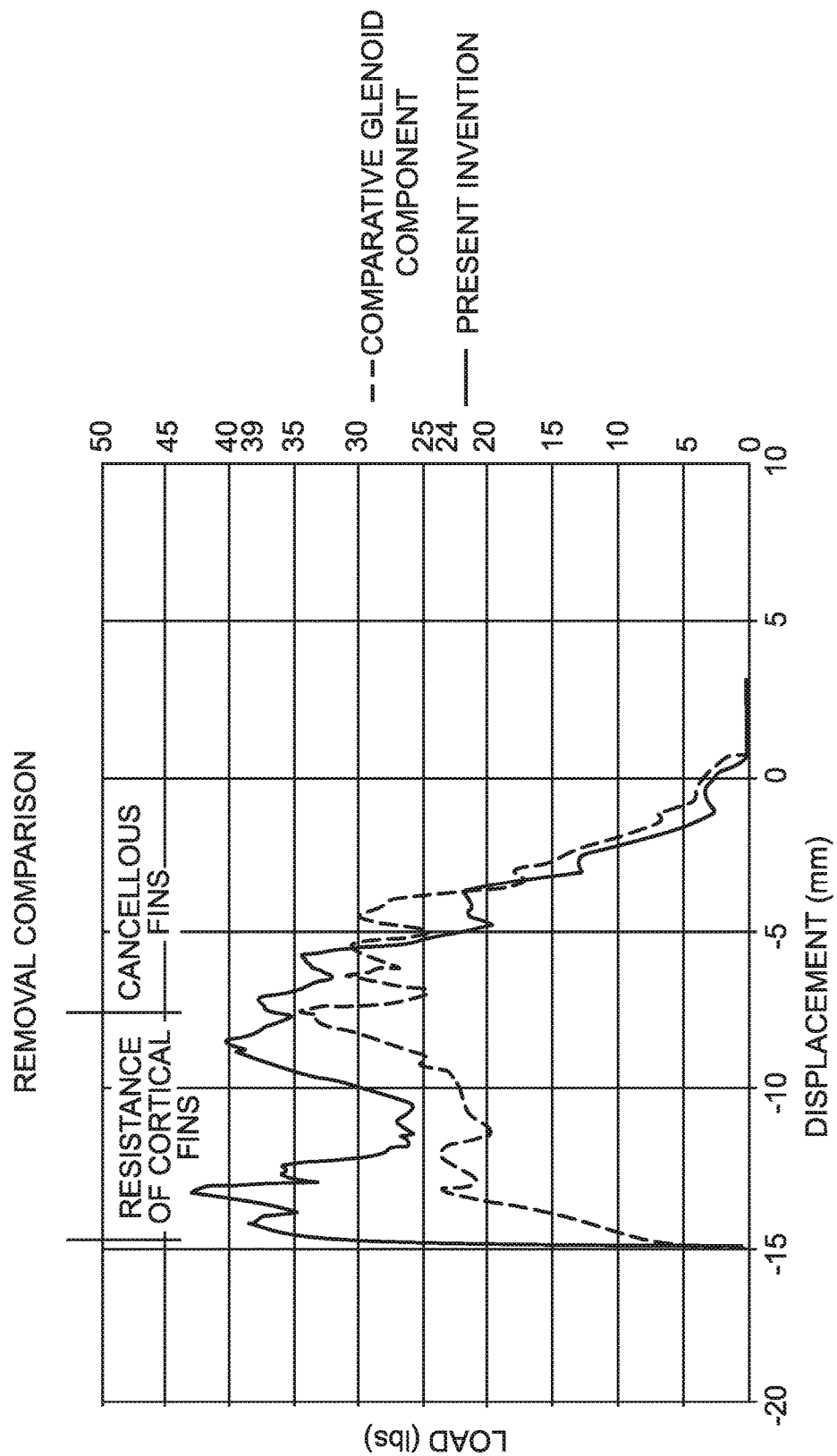
FIG. 12 is a graph of load versus displacement during removal of the glenoid component in accordance with an embodiment of the present invention.

FIG. 12 illustrates the load versus displacement of the glenoid component of the present invention and the load versus displacement of the comparative glenoid component during removal from the foam structure.

As can be seen in FIG. 12, the initial force required to pull the glenoid component of the present invention out from the foam structure spiked to about 39 pounds in the first millimeter of displacement, followed immediately by a spike of about 43.5 pounds at about 2 millimeters of displacement. In particular, a force of about 39 pounds was required to pull the first proximal fin through the anchor hole and a force of about 43.5 pounds was required to pull the second proximal fin through the anchor hole. These spikes all occurred within about 2 millimeters of displacement of the glenoid component of the present invention.

By contrast, the initial force required to move the comparative glenoid component relative to the foam structure increased more gradually, and only to an initial force of about 24 pounds within about 2 millimeters of displacement. It was not until the comparative glenoid component was displaced about 7.5 millimeters that the first distal fin engaged the anchor hole and increased the removal force to about 34 pounds.

As a practical matter, once the comparative glenoid component was displaced about 7.5 millimeters, the structural integrity of the prosthesis was compromised. The spike of about 34 pounds at 7.5 millimeters of displacement was too late to save the implant.

The glenoid component of the present invention provided a force about 71.5% greater than the comparative glenoid component, over less than half the displacement. As a result, the present glenoid component provided a significantly greater resistance to initial displacement than the comparative glenoid component.

Where a range of values is provided, it is understood that each intervening value, to the tenth of the unit of the lower limit unless the context clearly dictates otherwise, between the upper and lower limit of that range and any other stated or intervening value in that stated range is encompassed within the inventions. The upper and lower limits of these smaller ranges which may independently be included in the smaller ranges is also encompassed within the inventions, subject to any specifically excluded limit in the stated range. Where the stated range includes one or both of the limits, ranges excluding either both of those included limits are also included in the inventions.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present inventions are not entitled to antedate such publication by virtue of prior invention. Further, the dates of publication provided may be different from the actual publication dates which may need to be independently confirmed.

Other embodiments of the invention are possible. Although the description above contains many specificities, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims.

What is claimed is:

1. A method of fixating a glenoid prosthesis to a glenoid comprising:
    positioning the glenoid prosthesis adjacent the glenoid, the glenoid prosthesis comprising a head portion having a convex rear surface configured to engage with a glenoid and an articular surface configured to engage with a humeral component, and an anchor extending from said rear surface of the head portion;
    aligning an anchor of the glenoid prosthesis with a bore formed in the glenoid, wherein the anchor includes a first deformable fin and a second deformable fin; proximal of the first deformable fin;
    inserting the anchor in the bore such that the first deformable fin is implanted within cancellous bone; and
    further inserting the anchor into the bore until the second deformable fin is advanced past cortical bone and into the cancellous bone, a proximal-facing surface of the second deformable fin being spaced apart from the rear surface of the second head portion of the glenoid prosthesis by a distance generally corresponding to a thickness of the cortical bone,
    wherein when the rear surface of the head portion engages the glenoid, the proximal-facing surface of the second deformable fin directly engages with the cortical bone.

2. The method of claim 1 further comprising aligning at least one stabilizing pin of the glenoid prosthesis with at least one hole formed in the glenoid, wherein the stabilizing pin maintains the glenoid prosthesis in position relative to the glenoid.

3. The method of claim 2, further comprising inserting the at least one stabilizing pin of the glenoid prosthesis in the at least one hole formed in the glenoid.

4. The method of claim 3, further comprising securing the at least one stabilizing pin of the glenoid prosthesis in the at least one hole through a press fit or an interference fit.

5. The method of claim 3, further comprising securing the at least one stabilizing pin of the glenoid prosthesis in the at least one hole with bone cement.

6. The method of claim 5, wherein the bone cement is filled in an opening of the at least one stabilizing pin of the glenoid prosthesis.

7. The method of claim 2, wherein a drill guide is used to form the bore in the glenoid configured to receive the anchor of the glenoid prosthesis or the at least one hole in the glenoid configured to receive the at least one stabilizing pin of the glenoid prosthesis.

8. The method of claim 1, wherein the anchor has a tapered tip to facilitate insertion of the anchor into the bore.

9. The method of claim 1, wherein the first and second deformable fins are separable from the anchor.

10. The method of claim 9, further comprising positioning a spacer between the first and second deformable fins to adjust an offset between the first and second deformable fins.

11. The method of claim 1, wherein the bore is positioned substantially in the center of the surface of the glenoid.

* * * * *

UNITED STATES PATENT AND TRADEMARK OFFICE
CERTIFICATE OF CORRECTION

PATENT NO.       : 10,524,922 B2
APPLICATION NO.  : 15/379359
DATED            : January 7, 2020
INVENTOR(S)      : Robert Courtney, Jr. et al.

Page 1 of 1

It is certified that error appears in the above-identified patent and that said Letters Patent is hereby corrected as shown below:

On the Title Page

On page 2, Column 2, item (56), Other Publications, Line 1, delete "Countless" and insert --Cementless--.

In the Claims

Column 14, Line 41, Claim 1, delete "an" and insert --the--.

Column 14, Line 43, Claim 1, delete "fin;" and insert --fin--.

Column 14, Line 51, Claim 1, after "the" delete "second".

Column 14, Line 57, Claim 2, after "1" insert --,--.

Signed and Sealed this
Thirty-first Day of March, 2020

Andrei Iancu
*Director of the United States Patent and Trademark Office*